(12) United States Patent
Petrasek et al.

(10) Patent No.: US 11,541,094 B2
(45) Date of Patent: Jan. 3, 2023

(54) FORMULATIONS FOR TREATING METABOLIC SYNDROME AND INCREASING ENERGY LEVELS

(71) Applicant: Healthrite Partners, LLC, Redondo Beach, CA (US)

(72) Inventors: Danny Petrasek, Los Angeles, CA (US); Ferid Murad, Menlo Park, CA (US)

(73) Assignee: HealthRite Partners, LLC, Manhattan Beach, CA (US)

( * ) Notice: Subject to any disclaimer, the term of this patent is extended or adjusted under 35 U.S.C. 154(b) by 0 days.

(21) Appl. No.: 16/984,610

(22) Filed: Aug. 4, 2020

(65) Prior Publication Data

US 2021/0038672 A1 Feb. 11, 2021

Related U.S. Application Data

(60) Provisional application No. 62/883,270, filed on Aug. 6, 2019.

(51) Int. Cl.

| | |
|---|---|
| *A61K 36/736* | (2006.01) |
| *A61K 36/9066* | (2006.01) |
| *A61K 31/375* | (2006.01) |
| *A61K 31/733* | (2006.01) |
| *A23L 29/00* | (2016.01) |
| *A61K 36/87* | (2006.01) |
| *A23L 33/00* | (2016.01) |
| *A23L 33/105* | (2016.01) |
| *A23L 33/15* | (2016.01) |
| *A61K 31/05* | (2006.01) |

(52) U.S. Cl.
CPC .......... *A61K 36/736* (2013.01); *A23L 29/035* (2016.08); *A23L 33/105* (2016.08); *A23L 33/15* (2016.08); *A23L 33/30* (2016.08); *A61K 31/05* (2013.01); *A61K 31/375* (2013.01); *A61K 31/733* (2013.01); *A61K 36/87* (2013.01); *A61K 36/9066* (2013.01)

(58) Field of Classification Search
None
See application file for complete search history.

(56) References Cited

U.S. PATENT DOCUMENTS

| 2015/0140031 A1* | 5/2015 | Wood .................. A61K 9/0095 424/195.17 |
| 2016/0303177 A1 | 10/2016 | Bailey |
| 2018/0078601 A1 | 3/2018 | Mastaloudis et al. |
| 2018/0185432 A1 | 7/2018 | Alamdari et al. |

FOREIGN PATENT DOCUMENTS

| EP | 1137 429 B1 | 3/2005 |
| WO | WO 2018/142328 A1 | 8/2018 |

OTHER PUBLICATIONS

Alba et al. (2019) Crit. Rev. Food Sci. Nutr. vol. 59, No. 4: 626-638. (Year: 2019).*
Azhdari et al. (2019) Phytotherapy Research 33: 1289-1301. (Year: 2019).*
Casedas et al. (2016) Food Funct. 7: 4675-4682. (Year: 2016).*
Desai et al. (2021) Eur. J. Nutr. 60: 1587-1603. (Year: 2021).*
Farag et al. (2019) Clin. Nutrition Expertimental 26: 23-33. (Year: 2019).*
Ford et al. (2003) Diabetes vol. 52: 2346-2352. (Year: 2003).*
Godala et al. (2016) Menopause Rev. 15(1): 32-38. (Year: 2016).*
Guo et al. (2021) Frontiers in Nutrition vol. 8: (11 pages). (Year: 2021).*
Johnson (2020) J. Med. Food 23(12): 1238-1247. (Year: 2020).*
Lachin (2014) Recent Patents on Endocrin, Metabolic and Immune Drug Discovery vol. 8, No. 1: 67-74. (Year: 2014).*
Marin et al. (2018) Food Funct. 9: 5290-5300. (Year: 2018).*
Nemes et al. (2019) Nutrients 11: 1966 (17 pages) (Year: 2019).*
Vitale et al. (2017) Current Sports Medicine Reports vol. 16, No. 4: 230-239. (Year: 2017).*
Wong et al. (2020) Int. J. Med. Sci. vol. 17: 1625-1638. (Year: 2020).*
Yang et al. (2014) Phytotherapy Research 28: 1770-1777. (Year: 2014).*
Zhang et al. (2013) Evidence-Based Complementary and Alternative Medicine vol. 2013 (16 pages). (Year: 2013).*
Ataie-Jafari et al., "Effects of Sour Cherry Juice on Blood Glucose and Some Cardiovascular Risk Factors Improvements in Diabetic Women," Nutrition & Food Science, vol. 38, No. 4, pp. 355-360, 2008.
Azzeh et al., "Vitamin C supplementation and serum uric acid: A reaction to hyperuricemia and gout disease," PharmaNutrition, vol. 5, pp. 47-51, 2017.
Bell, Phillip G., et al, "Clinical Studies Demonstrating Tart Cherry Extract Lowering Serum Uric Acid, Blood Pressure Triglycerides Anti-Inflammatory Biomarkers (C Reactive Protein and Others), Glucose Regulation and Weight Management," Journal of Functional Foods 11, 82-90, 2014.
Bell et al., "Montmorency Tart Cherry (*Prunus cerasus* L.) Concentrate Lowers Uric Acid, Independent of Plasma Cyanidin-3-O-Glucosiderutinoside," Journal of Functional Foods, vol. 11, pp. 82-90, 2014.
Bell et al., "The effects of Montmorency Tart Cherry Concentrate supplementation of Recovery following prolonged intermittent exercise", Nutrients, vol. 4, No. 441, pp. 1-11, 2016.

(Continued)

*Primary Examiner* — Russell G Fiebig
(74) *Attorney, Agent, or Firm* — Knobbe, Martens, Olson & Bear LLP

(57) ABSTRACT

Disclosed herein are formulations, methods, and kits of formulations for inhibiting, ameliorating, delaying the onset of, reducing the likelihood of, treating, and/or preventing metabolic syndrome, and/or increasing energy levels. The formulations have at least one extract from a tart cherry, at least one antioxidant vitamin, at least one polyphenolic compound, and at least one prebiotic. Also disclosed are methods of making the formulations.

6 Claims, 4 Drawing Sheets

(56) References Cited

OTHER PUBLICATIONS

Bell et al., Montmorency Cherries Reduce the oxidative stress and inflammatory responses to repeated days high intensity stochastic cycling, Nutrients, vol. 6, pp. 829-843, 2014.
Burkewitz, Kristopher, "AMPK at the Nexus of Energetics and Aging," Cell Metabolism Review 20, 10-25, Jul. 1, 2014.
Chai, Sheau C., et al., "Impact of Tart Cherry Juice on Systolic Blood Pressure and Low-Density Lipoprotein Cholesterol in Older Adults: a randomized controlled trial," Food Funct., 9, 3185, 2018.
Desai, Terun, et al., "Effects of Montmorency Tart Cherry Supplementation on Cardio-Metabolic Markers in Metabolic Syndrome Participants: a pilot study," Journal of Functional Foods 57, 286-298, 2019.
Cicerchi, Christina, et al., "Uric Acid-Dependent Inhibition of AMP Kinase Induces Hepatic Glucose Production in Diabetes and Starvation: Evolutionary Implications of the Uricase Loss in Hominids," FASEB L. 28(8): 3339-3350, Aug. 2014.
Connolly et al., Efficacy of a tart cherry juice blend in preventing the symptoms of muscle damage, BR J Sports Med, vol. 40, 2006, pp. 679-683.
DeBosch, Brian J., "Early-Onset Metabolic Syndrome in Mice Lacking the Intestinal Uric Acid Transporter SLC2A9," Nature Communications 5:4642, Aug. 7, 2014.
Feldman, Elaine B., "Hypertriglyceridemia in Gout," Circulation, vol. XXIX, 508-513 Apr. 1964.
Forman, John P., "Uric Acid and Insulin Sensitivity and Risk of Incident Hypertension," Arch Intern Med, vol. 169, No. 2, Jan. 26, 2009.
Gao, Xiang, MD., "Vitamin C Intake and Serum Uric Acid Concentration in Men," J Rheumatol. 35(9): 1853-1858, Sep. 2008.
Hardie, Grahame, D., et al., "AMPK—a Nutrient and Energy Sensor that Maintains Energy Homeostatis," Nat Rev Mol Cell Biol; 13(4): 251-262, Dec. 12, 2017.
Herzig, Sebastien, et al., "AMPK: Guardian of Metabolism and Mitochondrial Homeostasis," Nat Rev Mol Cell Biol, 19(2): 121-135, Feb. 2018.
Hester et al., "Efficacy of an Anthocyanin and Prebiotic blend on intestinal environment in obese male and femail subjects", Journal of Nutrition and metabolism, vol. 2018, in 11 pages.
Hirsch et al., "Allopurinol Acutely Increases ATP Energy Delivery in Failing Human Hearts," Journal of the American College of Cardiology, vol. 59, No. 9, pp. 802-808, 2012.
Howatson et al., "Influence of tart cherry juice on indices of recovery following marathon running" Scandinavian Journal of Medicine & Science in sports, vol. 20, pp. 843-852, 2010.
Huang, Han-Yao, et al., "The Effects of Vitamin C Supplementation on Serum Concentrations of Uric Acid," Arthritis & Rheumatism, vol. 52, No. 6, pp. 1843-1847, Jun. 2005.
Jacob, Robert A., "Consumption of Cherries Lowers Plasma Urate in Healthy Women," downloaded from https://academic.oup.com/in/article-abstract/133/6/1826/4688173, 2003.
Jayarathne et al., "Tart cherry reduces Inflammation in Adipose Tissue of Zucker fatty rats and cultured 2t3-L1 Adipocytes", Nutrients, vol. 10, No. 1576, pp. 1-16, 2018.
Johnson et al., "Shortage of Cellular ATP as a cause of Diseases and Strategies to Enhances ATP, Hypothesis and Theory Frontiers in Pharmacology," vol. 10, Article 98, 2018.
Juraschek, Stephen P., et al., "Effect of Oral Vitamin C Supplementation on Serum Uric Acid: a Meta-Analysis of Randomized Controlled Trials," Arthritis Care Res (Hoboken), 63(9): 1295-1306, Sep. 2011.
Kamatani et al., "Clinical Studies on Changes in Purine Compounds in Blood and Urine by the Simultaneous Administration of Febuxostat and Inosine, or by Single Administration of Each, Gout and Nucleic Acid Metabolism," vol. 41, No. 2, 2017.
Kanbay, Mehmet, et al., "Uric Acid in Metabolic Syndrome: From an innocent bystander to a central player," European Journal of Internal Medicine 29, 3-8, 2016.

Keane et al., "Effects of Montmorency Tart Cherry (L. *Prunus cerasus*) Consumption on Nitric Oxide Biomarkers and Exercise Performance," Scandinavian Journal of Medicine & Science in Sports, vol. 28, No. 7, pp. 1746-1756, 2018.
Keane et al., "Effects of Montmorency tart cherry (*Prunus cerasus* L.) consumption on vascular function in men with early hypertension", American Society for Nutrition, vol. 103, pp. 1531-1539, 2016.
Keane et al., "Montmorency Tart Cherries (*Prunus cerasus* L.) Modulate Vascular Function acutely, in the absence of improvement in cognitive performance," British Journal of Nutrition, 116, 1935-1944, 2016.
Keenan et al., "Relation of Uric Acid to Serum Levels of High-Sensitivity C-Reactive Protein, Triglycerides, and High Density Lipoprotein Cholesterol and to Hepatic Steatosis" American Journal of Cardiology, vol. 110, 2012, pp. 1787-1792.
Kelley et al.,"A review of the health benefits of cherries" Nutrients, vol. 10, pp. 1-22, 2018.
Kirakosyan, Ara, et al., "Chemical Profile and Antioxidant Capacities of Tart Cherry Products," Food Chemistry 2008.
Levers et al., "Effects of powdered Montmorency tart cherry supplementation on acute endurance exercise performance in aerobically trained individuals" Journal of the International Society of sports nutrition, vol. 13, No. 22, pp. 1-23, 2016.
Morgan et al., "Montmorency Cherry Supplementation Improves 15-Km Cycling Time-Trial Performance," European Journal of Applied Physiology, vol. 119, Issue 3, pp. 675-684, 2019.
Mule, Giuseppe, et al., "Hyperuciemia and High Blood Pressure at Rest and During Exericse: Guilty or Innocent? The Jury is Still Out," J Clin Hypertens. 20: 557-559, 2018.
Nakagawa, Takahiko, et al., "A causal role for uric acid in fructose-induced metabolic syndrome," Am J Physiol Renal Physiol 290: F625-F631, 2006.
Perez-Pozo, Se, "Excessive Fructose Intake Induces the Features of Metabolic Syndrom in Healthy Adult Men: role of uric acid in the hypertensive response," International Journal of Obesity, 34: 454-461, 2010.
Polley et al., "Tart cherry consumption with or without prior exercise increases antioxidant capacity and decreases triglyceride levels following a high fat meal" Appl Physiology Nutrition Metab, download from www.nrcreaserchpress.com printed in 2019 in 42 pages.
Rabello de Lima et al., Consumption of cherries as a strategy to attenuate exercise-induced muscle damage and inflammation in humans, Nutricion Hospitalaria, vol. 32, No. 5, 2015, pp. 1885-1893.
Reznick, Richard M., "The Role of AMP Activated Protein Kinase in Mitochondrial Biogenesis," Physiol 574.1 pp. 33-39, 2006.
Salminen, Antero, et al., "AMP Activated Protein Kinase (AMPK) Controls the Aging Process via an Integrated Signaling Network," Ageing Research Reviews 11, 230-241, 2012.
Schumacher et al., "Randomized double-blind crossover study of the efficacy of a tart cherry juice blend in treatment of osteoarthritis of the knee" Osteoarthritis and Cartilage, vol. 21, 2013, pp. 1035-1041.
Seymour, E. Mitchell, et al., "Anthocyanin Pharmacokinetics and dose-dependent plasma antioxidant pharmacodynamics following whole tart cherry intake in healthy humans," Journal of Functional Foods 11, 509-516, 2014.
Seymour et al., "Regular Tart Cherry Intake Alters Abdominal Adiposity, Adipose Gene Transcription, and Inflammation in Obesity-Prone Rats Fed a High Fat Diet," Journal of Medicinal Food, vol. 12, No. 5, pp. 935-942, 2009.
Tart Cherries. Summary of Current Scientific Literature, believed to be published in 2011.
Soletsky, Beth et al., "Uric Acid Reduction Rectifies Prehypertension in Obese Adolescents," downloaded from http://hyper.ahajournals.org/ on Mar. 7, 2018.
Srivastava, P.K., "Modeling the Drug Therapy for HIV Infection," Journal of Biological Systems, vol. 17, No. 2, pp. 213-223, 2009.
Stamp, Lisa K., "Clinically Insignificant Effect of Supplemental Vitamin C on Serum Urate in Patients with Gout," Arthritis and Rheumatism, vol. 65, No. 6, Jun. 2013, pp. 1636-1642, 2013.

(56) References Cited

OTHER PUBLICATIONS

Tiernan et al., "Tart cherry in amelioration of pain in the elderly" Nutrition and Aging, vol. 3, 2015, pp. 203-217.
Vitale et al., "Tart Cherry Juice in Athletes: A literature review and commentary" Nutrition and Ergogenic Aids, vol. 16, No. 4, 2017, pp. 230-239.
Yogalakshmi, Baskaran, "Grape Seed Proanthocyanidins and Metformin Act by Different Mechanisms to Promote Insulin Signaling in Rats Fed High Calorie Diet," J. Cell Commun. Signal, 8: 13-22, 2014.

* cited by examiner

FORMULATIONS FOR TREATING METABOLIC SYNDROME AND INCREASING ENERGY LEVELS

PRIORITY AND CROSS-REFERENCE TO RELATED APPLICATIONS

This application claims the benefit of U.S. Provisional Application No. 62/883,270, filed Aug. 6, 2019. Any and all applications for which a foreign or a domestic priority is claimed is/are identified in the Application Data Sheet filed herewith and is/are hereby incorporated by reference in their entireties.

FIELD

The present disclosure is generally related to formulations, methods, and kits of formulations for inhibiting, ameliorating, delaying the onset of, reducing the likelihood of, treating, and/or preventing metabolic syndrome, and/or increasing energy. The present disclosure is also related to methods of making the formulations.

BACKGROUND

Metabolic Syndrome (sometimes referred to as the obesity epidemic or prediabetes) is a clinical condition that affects 1 in 3 adults and 1 in 5 children in the USA and other industrialized countries.

SUMMARY

In some embodiments, a formulation for inhibiting, ameliorating, delaying the onset of, reducing the likelihood of, treating, and/or preventing metabolic syndrome and/or increasing energy levels is provided. In some embodiments, the formulation comprises at least one extract from a tart cherry, at least one antioxidant vitamin, at least one polyphenolic compound, and at least one prebiotic. In some embodiments of the formulation, the at least one extract from a tart cherry is from Montmorency cherries, Balaton cherries, or a combination thereof. In some embodiments of the formulation, the at least one antioxidant vitamin is Vitamin C. In some embodiments of the formulation, the at least one polyphenolic compound is selected from the group consisting of turmeric, and resveratrol. In some embodiments of the formulation, the at least one polyphenolic compound has antioxidant properties, anti-inflammatory properties, or a combination thereof. In some embodiments of the formulation, the at least one prebiotic is inulin.

In some embodiments, a formulation comprises an effective amount of at least one extract from a tart cherry, an effective amount of at least one antioxidant vitamin, an effective amount of at least one polyphenolic compound, and an effective amount of at least one prebiotic, wherein the effective amount of each ingredient is sufficient in combination for inhibiting, ameliorating, delaying the onset of, reducing the likelihood of, treating, and/or preventing metabolic syndrome, and/or increasing energy levels. In some embodiments of the formulation, the effective amount of the at least one extract from a tart cherry ranges from about 1.5 grams to about 2.5 grams. In some embodiments of the formulation, the effective amount of the at least one antioxidant vitamin ranges from about 250 mg to about 500 mg. In some embodiments of the formulation, the effective amount of the at least one polyphenolic compound ranges from about 25 mg to about 200 mg. In some embodiments of the formulation, the effective amount of the at least one prebiotic is about 450 mg.

In some embodiments of the formulation, the at least one extract from a tart cherry is from Montmorency cherries, Balaton cherries, or a combination thereof. In some embodiments of the formulation, the at least one antioxidant vitamin is Vitamin C. In some embodiments of the formulation, the at least one polyphenolic compound is selected from the group consisting of turmeric, resveratrol, and grape seed oil extract. In some embodiments of the formulation, the at least one polyphenolic compound has antioxidant properties, anti-inflammatory properties, or a combination thereof. In some embodiments of the formulation, the at least one prebiotic is inulin.

In some embodiments of the formulation, the effective amount of vitamin C ranges from about 250 mg to about 500 mg. In some embodiments of the formulation, the effective amount of turmeric is about 25 mg. In some embodiments of the formulation, the effective amount of grape seed oil extract is about 200 mg. In some embodiments of the formulation, the effective amount of inulin is about 450 mg.

In some embodiments, a method for inhibiting, ameliorating, delaying the onset of, reducing the likelihood of, treating, and/or preventing metabolic syndrome, and/or increasing energy levels in a subject is provided. In some embodiments, the method comprising administering a formulation comprising an effective amount of at least one extract from a tart cherry, an effective amount of at least one antioxidant vitamin, an effective amount of at least one polyphenolic compound, and an effective amount of at least one prebiotic, wherein the effective amount of each ingredient is sufficient in combination for inhibiting, ameliorating, delaying the onset of, reducing the likelihood of, treating, and/or preventing metabolic syndrome, and/or increasing energy levels.

DETAILED DESCRIPTION

Figure 1:
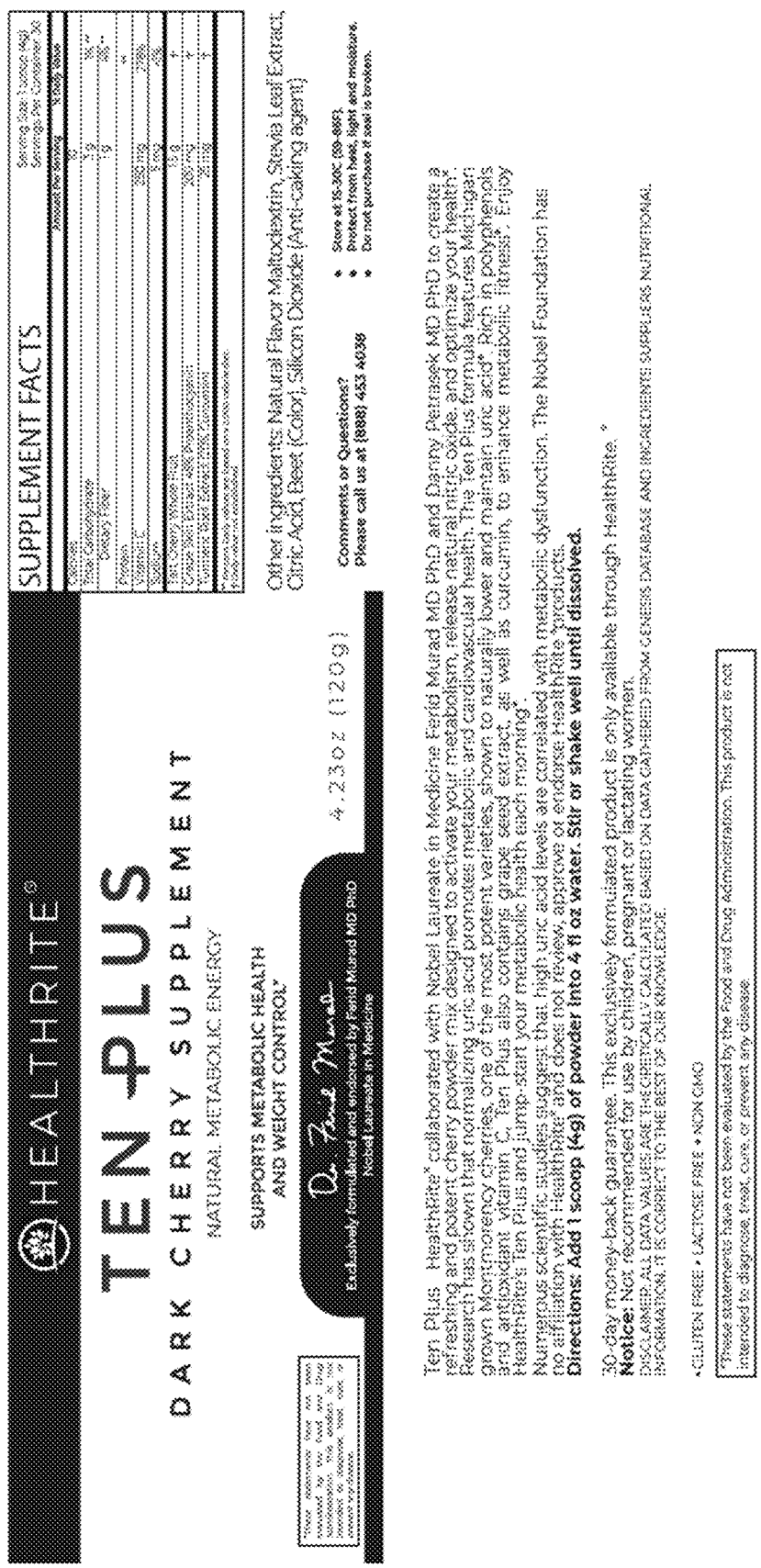
FIG. 1 shows an embodiment of a label for an embodiment of a formulation (referred to as Ten Plus) provided herein.

Metabolic Syndrome is considered to be present when a subject based on established clinical criteria. Metabolic syndrome is a set of clinical conditions that occur together and is associated with an increased risk of heart disease, stroke and type 2 diabetes. The conditions include elevated blood pressure, elevated blood glucose, excess body fat, abnormal cholesterol and/or triglyceride levels, and elevated uric acid levels.

The clinical criteria for the diagnosis of metabolic syndrome, as defined in the National Cholesterol Education Program's Adult Treatment Panel III (ATP III) report (which is hereby included by reference in its entirety), include waist circumference of more than 102 cm (40 in) in men and more than 88 cm (35 in) in women; triglyceride levels of at least 150 mg per dL (1.70 mmol per L); high-density lipoprotein cholesterol levels of less than 40 mg per dL (1.04 mmol per L) in men and less than 50 mg per dL (1.30 mmol per L) in women; blood pressure of at least 130/85 mm Hg; and fasting glucose levels of at least 110 mg per dL (6.10 mmol per L) (Table 1).

leading to "fatty liver" (AMPK probably plays a central role in preventing or permitting the development of fatty liver),

TABLE 1

Definitions of metabolic syndrome

|  | NCEP ATP III (2005 REVISION) | WHO (1998) | EGIR (1999) | IDF (2005) |
|---|---|---|---|---|
| Absolutely required | None | Insulin resistance* (IGT, IFG, T2D or other evidence of IR) | Hyperinsulinemia$^\pm$ (plasma insulin >75$^{th}$ percentile) | Central obesity (waist circumference$^\#$) ≥94 cm (M), ≥80 cm (F) |
| Criteria | Any three of the five criteria below | Insulin resistance or diabetes, plus two of the five criteria below | Hyperinsulinemia, plus two of the four criteria below | Obesity, plus two of the four criteria below |
| Obesity | Waist circumference: >40 inches (M), >35 inches (F) | Waist/hip ratio: >0.90 (M), >0.85 (F); or BMI >30 kg/m$^2$ | Waist circumference: ≥94 cm (M), ≥80 cm (F) | Central obesity already required |
| Hyperglycemia | Fasting glucose ≥100 mg/dl or Rx | Insulin resistance already required | Insulin resistance already required | Fasting glucose ≥100 mg/dl |
| Dyslipidemia | TG ≥150 mg/dl or Rx | TG ≥150 mg/dl or HDL-C: <35 mg/dl (M), <39 mg/dl (F) | TG ≥177 mg/dl or HDL-C <39 mg/dl | TG ≥150 mg/dl or Rx |
| Dyslipidemia (second, separate criteria) | HDL cholesterol: <40 mg/dl (M), <50 mg/dl (F); or Rx |  |  | HDL cholesterol: <40 mg/dl (M), <50 mg/dl (F); or Rx |
| Hypertension | >130 mmHg systolic or >85 mmHG diastolic or Rx | ≥140/90 mmHg | ≥140/90 mmHg or Rx | >130 mmHg systolic or >85 mmHG diastolic or Rx |
| Other criteria |  | Microalbuminuria$^1$ |  |  |

*IGT, impaired glucose tolerance; IFG, impaired fasting glucose; T2D, type 2 diabetes; IR, insulin resistance; other evidence includes euglycemic clamp studies.
$^1$Urinary albumin excretion of ≥20 μg/min or albumin-to-creatine ration of ≥30 mg/g.
$^\pm$Reliable only in patients without T2D.
$^\#$Criteria for central obesity (waist circumference) are specific for each population; values given are for European men and women. Rx, pharmacologic treatment.

The etiology of the syndrome is believed to be related to at least three general features that may be interrelated: insulin resistance, dysregulation of adipose physiology and inflammation.

The prevalence of the metabolic syndrome parallels the prevalence of Type II Diabetes (DM II) and has been increasing at an accelerated rate. The incidence of DM II was in the range of 1-2% of the population at the beginning of the 20th century and currently it is estimated to be close to 10% of the population. The metabolic syndrome classification was an eventual outcome of the Framingham study to determine cardiovascular risk factors. Motivated by the death of FDR from malignant hypertension in 1945, Harvard Medical school initiated a government sponsored program, in the town of Framingham Massachusetts, in order to establish risk factors for cardiovascular disease. The Framingham study established 4 metabolic risk factors (1958): Hypertension, Diabetes, hyperlipidemia and obesity (smoking was a non-metabolic factor). The fact that 3 or 4 of these factors often appeared in the same subject was noted in the literature and in 1988 Prof Gerald Reavan from Stanford popularized the term Metabolic Syndrome. The consensus was that insulin resistance was the underlying condition that precipitated the features of the syndrome. Approximately 10 years later work by Graham and Hardie and others showed/implicated that a metabolic switch (AMPK) was central to all the features seen in Metabolic syndrome. AMPK is an energy sensor (enzyme) in all cells that is activated/deactivated when the ratio of ATP/AMP is decreased/increased. When AMPK is activated the body is in catabolic or fat burning mode. Conversely when AMPK is inactive the body is in fat storage mode.

The current clinical thinking in terms of the sequence of events that leads to the metabolic syndrome is likely the following:
over-nutrition or perhaps inappropriate nutrition (high fructose corn syrup as an example to be further elucidated below);
leading to insulin resistance,
leading to obesity,
leading to diabetes, hypertension, and hyperlipidemia.

The process may be further amplified by an inflammatory component that is generated by nonalcoholic steatohepatitis ("NASH") or obesity itself.

Separate from the work of AMPK in metabolic syndrome is the contribution of AMPK in improving fitness, endurance and athletic performance. Major pharmaceutical companies have even attempted to create a performance enhancing agonist of AMPK called AICAR. The results were sufficiently compelling that the world anti-doping federation declared it a banned substance.

Figure 2:
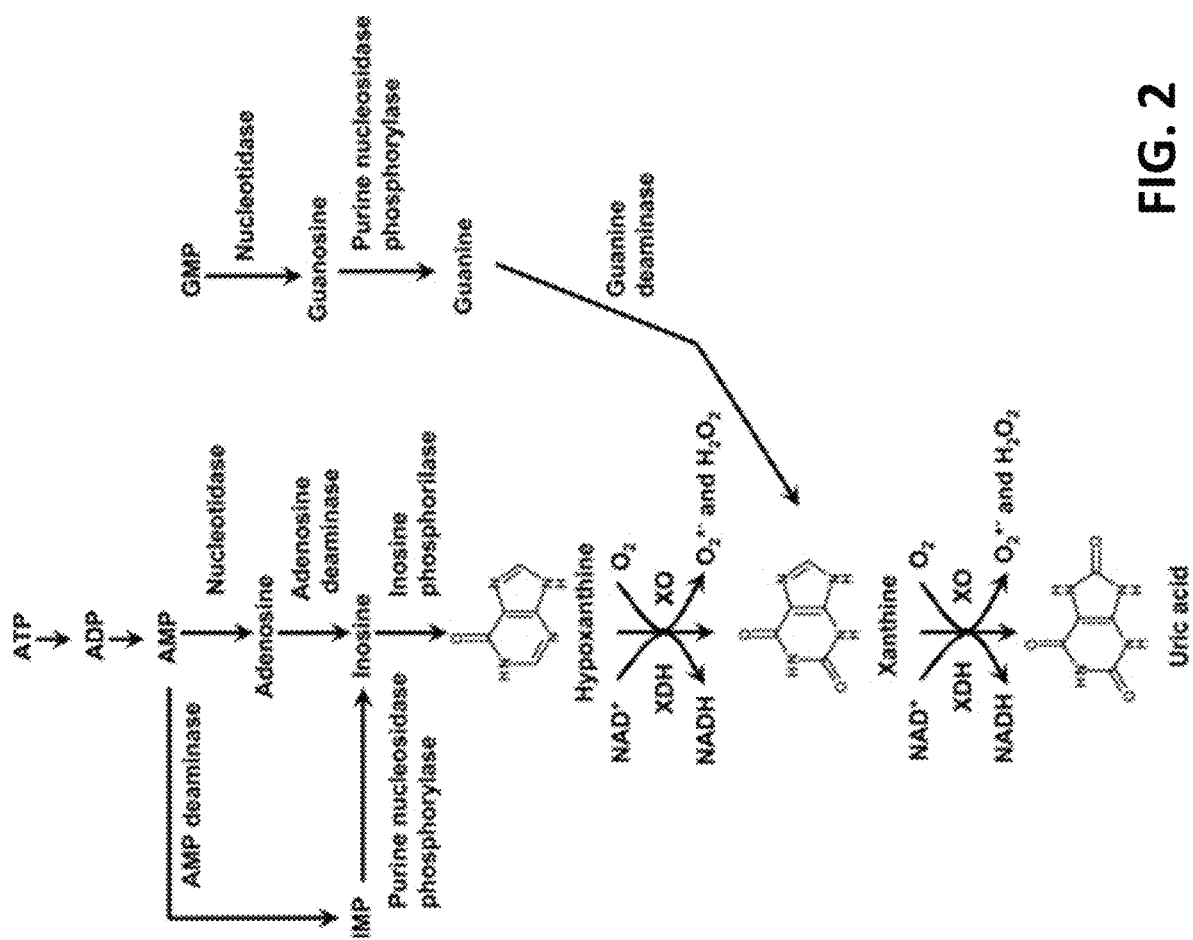
FIG. 2 shows generation of uric acid via the purine metabolism pathway.

In parallel, elevated uric acid had been associated with all aspects of the metabolic syndrome. The contribution of uric acid in this pathology is not obvious. Uric acid is an end product of purine metabolism (FIG. 2). Endogenous sources of purine are ATP (clearly connecting to the previous discussion of AMPK) and GTP.

Exogenous sources are sugar and beer. Sugar which is disaccharide composed of fructose and glucose. Fructose has the unique property of actually using up or depleting ATP prior to helping create it in the mitochondrial citric acid cycle.

There are two biochemical pathways to generate ATP.

De novo synthesis as a result of using carbohydrates (glycolysis), lipids (fatty oxidation) and amino acids as substrates converging to a common mechanism (tricarboxylic acid cycle) in the mitochondria and resulting in the generation of ATP.

Figure 3:
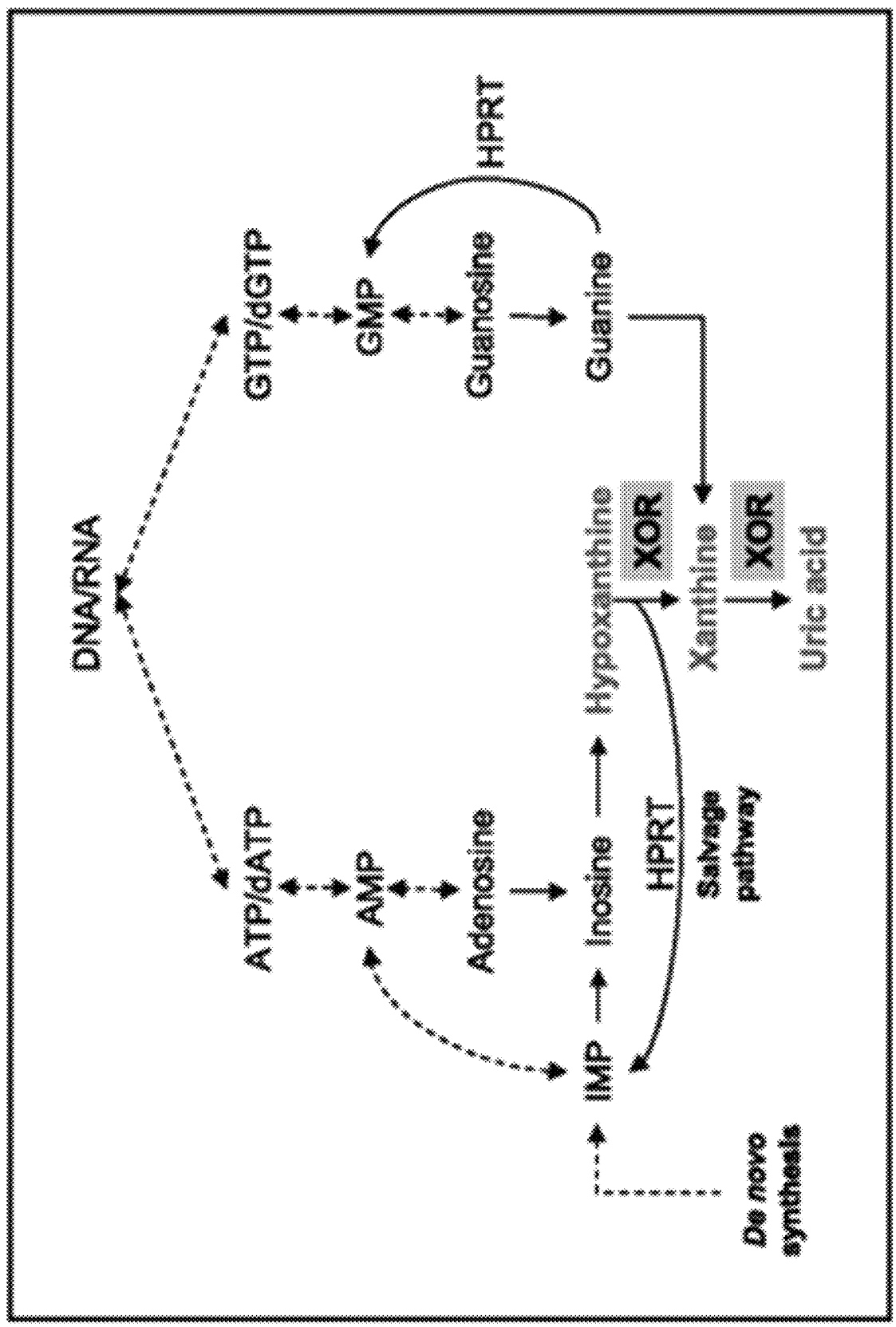
FIG. 3 shows generation of uric acid via the salvage pathway.

The second pathway is often referred to as the Salvage pathway (FIG. 3). When ATP is used to provide energy in cellular processes it is degraded to ADP then AMP then Inosine and eventually Uric acid.

The salvage pathway refers to the creation of ATP by reversal of the degradation cascade and using the degradation products to build the ATP molecule back up.

Without being limited by any particular theory, when pharmaceutical agents such as Allopurinol or Febuxostat (both Xanthine oxidase inhibitors) are used to block the conversion of hypoxanthine and xanthine to uric acid, there is an increase in cellular ATP. Several studies have shown this result including in clinical studies in humans.

In addition, it is interesting to note that there exists a synergistic effect in increasing ATP in the cell by combining Inosine with Febuxostat. Inosine alone did not affect ATP levels but in combination with Febuxostat increased ATP levels beyond levels of Febuxostat alone. Inosine (as seen below in both diagrams) is a degradation product of ATP and can be used by salvage to make more ATP.

Figure 4:
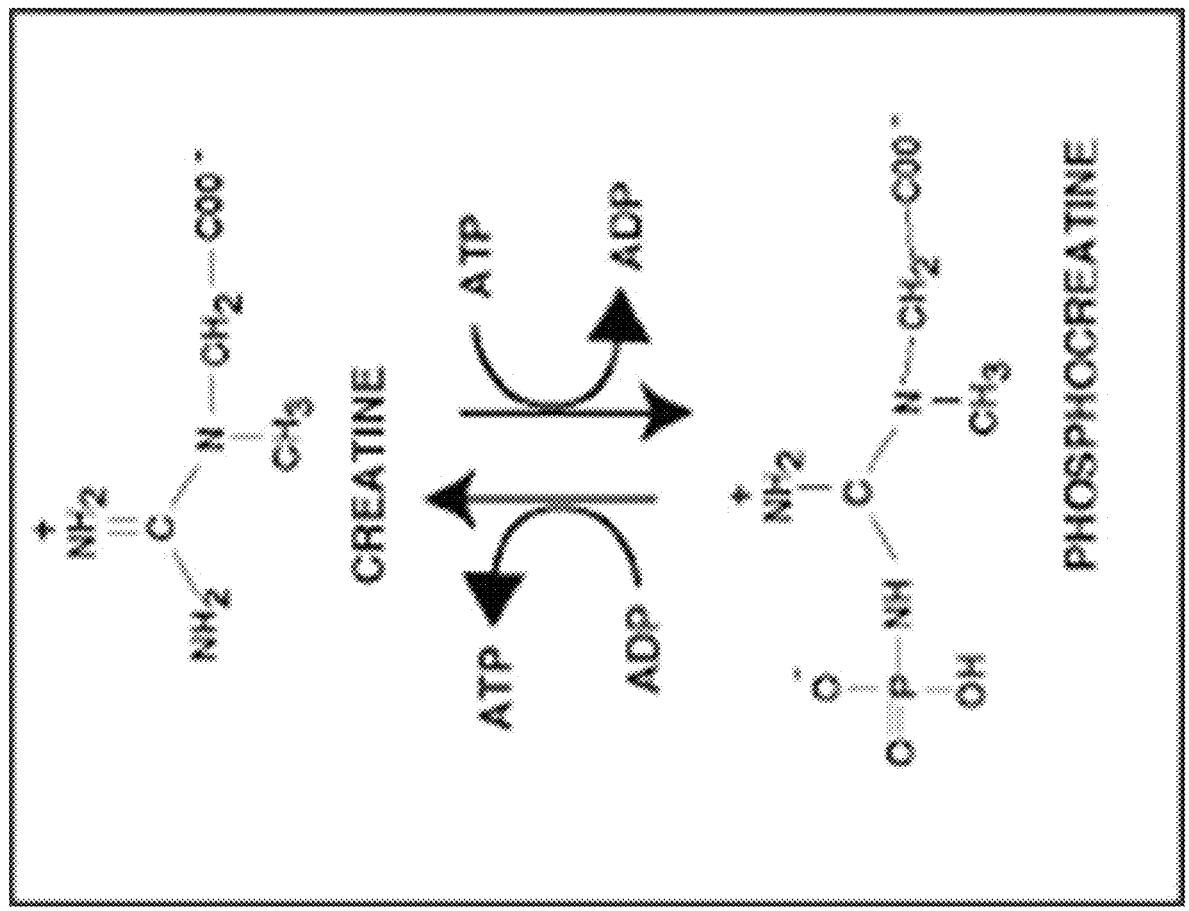
FIG. 4 shows generation of ATP from phosphocreatine.

Finally, a last ingredient to compliment ATP production is phosphocreatine. Phosphocreatine facilitates the creation of ATP from ADP (FIG. 4) and is an additional non-overlapping pathway leading to increase cell ATP and thus energy.

A side chain of fructose metabolism actually generates uric acid. The uric acid is believed to indirectly and directly inactive AMPK and therefor contribute to fatty liver and insulin resistance leading to metabolic syndrome. There exist numerous peer reviewed articles that support this thesis including genetic and molecular cell biology as well as clinical trials. Humans and primates are the only mammals that have a high uric acid level and in general the only species that naturally develop metabolic syndrome. All other mammals possess an enzyme, uricase, which dissolves uric acid. Our biological ancestors lost the uricase gene 15 million years ago in the Miocene global cooling. Prior to that these biological ancestors ate fruit as a primary source of food. With global cooling tropical forests dried up as did the food supply. Loss of the uricase gene promoted a high uric acid level permitting fast and efficient fat storage and enabling the species to survive at least a month without food. This conferred a survival advantage when food was scarce but became a disadvantage when nutrition is available 24 hours a day. Thus, giving the basis for the obesity epidemic we now witness where processed foods that are enriched with high fructose corn syrup is heavily used. As an interesting demographic proof of this concept are the Maori of New Zealand who have both the highest incidence of gout (high uric acid) in the world as well as the highest rate of metabolic syndrome (80% of the population).

The medical research that encompasses the discussion above resides in three largely independent domains: 1) uric acid and metabolic syndrome, 2) AMPK and metabolic syndrome, athletic performance, endurance and recovery, and 3) inflammation and its role in metabolic syndrome and recovery.

As a matter of background, "cardio exercise" is known to reduce insulin resistance improve hypertension and also activate AMPK. AMPK induces a long list of cascading events including but not limited to activation of nitric oxide pathways, lipid catabolism and mitochondrial biogenesis.

A standard therapy employed in combating insulin resistance is Metformin (prescription RX). Metformin likely works by disrupting "complex I" of the electron transport chain and indirectly activating AMPK. Other therapeutics have also been shown to influence AMPK. Aspirin activates AMPK, as well as reducing inflammation via the COX pathway. Recently, allopurinol (a xanthine oxidase inhibitor that reduces uric acid levels) has also been shown to affect elements of metabolic syndrome.

For hundreds of years cherries have been used as a natural remedy to treat gout: an arthritic condition that is a result of uric acid crystals in the joint space. Several studies demonstrate that tart cherries can reduce serum levels of uric acid as well as other markers of inflammation such as CRP and sedimentation rate. The biochemistry that underlies the effect is twofold. An inhibition of the enzymes that generate uric acid as well as an anti-inflammatory effect on the COX pathway. The effect is likely due to the concentration of anthocyanins and phenolics in the specific cultivar or type of cherry.

There is a large and separate body of literature that has studied the use of tart cherries as improving endurance, performance and recovery in athletics. The cultivars used are generally speaking Montmorency cherries, known for high anthocyanin and phenolic levels. A large majority of these studies show significant improvement in endurance performance and recovery and some of these studies are double-blinded placebo-controlled crossover designed. Further evidence of the mechanism is that in the few studies that had negative outcomes, the dosage used was insufficient to lower the uric acid.

There are some studies that have tested tart cherries as improving aspects of metabolic health including a recent pilot study showing a lowering of insulin resistance. However even in these studies, the underlying mechanism of uric acid is never invoked.

Without being limited by any particular theory, Tart cherry (Montmorency and Balaton cultivars) are known to have the highest levels of phenolics and anthocyanins. However, the anthocyanin I, II, and Phenolic concentrations have not been fully established.

High anthocyanin, high polyphenolic Tart cherries such as Montmorency and Balaton have been shown to reduce uric acid by inhibiting xanthine oxidase (XO).

Lowering uric acid can increase cellular ATP in 2 ways.
The enzyme AMPK is known as the master metabolic sensor. Active AMPK generates de novo ATP from fat, carbohydrates etc. Uric acid inhibits AMPK. Lowering uric acid modestly nonlinearly increases AMpk activity and thus increase ATP.
Lowering uric acid production by inhibiting XO also increases the Purine salvage pathway which independently increases ATP.

As an additional point of differentiation, Tart Cherry also inhibits COX I and II enzymes that are responsible for generating proinflammatory molecules.

There is a strong relationship between inflammation and cell energetics. The anti-inflammatory component of tart cherries is a positive physiological attribute with respect to energy production and as such can be regarded as having energy benefits beyond other XO inhibitors.

There is a need for a formulation for inhibiting, ameliorating, delaying the onset of, reducing the likelihood of, treating, and/or preventing metabolic syndrome, and/or increasing energy levels.

Formulations and Methods

The present disclosure is related to formulations for inhibiting, ameliorating, delaying the onset of, reducing the likelihood of, treating, and/or preventing metabolic syndrome, and/or increasing energy levels. Besides metabolic syndrome, The formulations are intended to improve fitness-related end points, including performance, endurance, recovery and/or energy levels. An embodiment of the formulations according to the present disclosure is referred to as Ten Plus. An embodiment of Ten Plus is provided in the form of a dark cherry supplement. An embodiment of Ten Plus is provided in the form of a dark cherry supplement, which provides natural metabolic energy. An embodiment of Ten Plus is provided in the form of a dark cherry supplement, which provides natural metabolic energy, and supports metabolic health. An embodiment of Ten Plus is provided in the form of a dark cherry supplement, which provides natural metabolic energy, and supports weight control. An embodiment of Ten Plus is provided in the form of a dark cherry supplement, which supports metabolic health and weight control. An embodiment of Ten Plus is provided in the form of a dark cherry supplement, which provides natural metabolic energy, and supports metabolic health and weight control. An embodiment of a label of Ten Plus is shown in FIG. 1

In some embodiments, the formulations comprise at least one/one or more tart cherry extract from Montmorency cherries, Balaton cherries, or a mixture of Montmorency and Balaton cherries. The formulations additionally and/or optionally comprise one or more antioxidant vitamins, one or more polyphenolic compounds with antioxidant and/or anti-inflammatory properties, and one or more prebiotics. In some embodiments, the one or more antioxidant vitamins includes beta-carotene, vitamin C, and vitamin E. In some embodiments, the one or more polyphenolic compounds with antioxidant and/or anti-inflammatory properties include curcumin, resveratrol, flavonoids, flavanols, flavonols, flavonones, flavones, isoflavones, anthocyanins, lignans, stilbenes, and the like. In some embodiments, the resveratrol is obtained from an extract of grape seed, grape seed oil, or grape skin. In some embodiments, the one or more prebiotics include inulin. Non-limiting examples of sources of prebiotic can include chicory root, garlic, dandelion greens, Jerusalem artichoke, onions, leeks, asparagus, bananas, barley, oats, apples, Konjac root, cocoa, Burdock root, flax seeds, Yacon root, jicama root, wheat bran, and seaweed. In some embodiments, the formulations further comprise one or more of inosine, and creatine.

Disclosed herein are embodiments of formulations comprising various combinations of Tart cherry, Vitamin C, Turmeric (Curcumin), Inulin, and Grape seed extract for inhibiting, ameliorating, delaying the onset of, reducing the likelihood of, treating, and/or preventing metabolic syndrome, and/or increasing energy levels. In some embodiments, the formulations comprising various combinations of Tart cherry, Vitamin C, Turmeric (20% Curcumin), Inulin, and Grape seed extract are for inhibiting, ameliorating, delaying the onset of, reducing the likelihood of, treating, and/or preventing metabolic syndrome. In some embodiments, the formulations comprising various combinations of Tart cherry, Vitamin C, Turmeric (20% Curcumin), Inulin, and Grape seed extract are for increasing energy levels. In some embodiments, the formulations comprising various combinations of Tart cherry, Vitamin C, Turmeric (20% Curcumin), Inulin, and Grape seed extract are for both inhibiting, ameliorating, delaying the onset of, reducing the likelihood of, treating, and/or preventing metabolic syndrome, and/or increasing energy levels.

In some embodiments, the formulation is an oral supplement. In some embodiments, the formulation is an edible solid or an edible semi-solid. In some embodiments, the formulation is a potable liquid. In some embodiments, the formulation is a powder or pellet that can be reconstituted in a potable liquid (e.g., water). In some embodiments, the formulation is a tablet or a capsule that can be taken without reconstitution.

Embodiments of the formulations provided herein comprise active ingredients, inactive ingredients, excipients, additives, and/or pharmaceutically acceptable carriers. Examples of additives include natural polymer compounds, inorganic salts, binders, lubricants, disintegrants, surfactants, thickeners, coating agents, pH adjusters, antioxidants, flavoring agents, preservatives, and colorants among others. Examples of other pharmaceutically acceptable carriers include liquid carriers such as water, alcohol, emulsion, and solid carriers such as gel, powder, etc. Standard pharmaceutical formulation techniques and ingredients can be used, such as those disclosed in Remington's The Science and Practice of Pharmacy, 21st Ed., Lippincott Williams & Wilkins (2005), which is hereby incorporated by reference in its entirety.

Embodiments of the formulations for oral administration can be any dosage form that is suitable for oral ingestion, for example, liquid formulations such as elixir, suspension, syrup, emulsion, ampoule, a premixed ready-to-consume drink, etc., solid formulations such as gel, gum, drop, powder, granule, pill, sugar-coated tablet, film-coated tablet, capsule, package agent, etc. Also contemplated are sustained-release formulations such as gel-coated formulations, multi-coated formulations, localized release formulations.

In some embodiments, the formulation is provided in the form of a tablet, capsule, gel cap, or softgel. The tablet, capsule, gel cap, or softgel may comprise additional inactive ingredients such as fillers including, but not limited to, rice flour, methylcellulose, magnesium stearate. Several tablets, capsules, gel caps, or softgels typically comprise one daily dose of each of the active ingredients, as described below.

In some embodiments, the formulation is a single serving formulation to be taken once per day by a subject. Thus, in some embodiments a daily dose of active ingredients is provided in a single serving. In some embodiments one daily dose may be divided among two or more servings to be taken in a day, for example among two or more servings of a liquid beverage or two or more tablets. A daily dose of the formulation can be taken by or administered to a subject in a 24 hour period. In some embodiments, a daily dose of the formulation is taken every day for 1 week to 12 months. In some embodiments, the formulation is taken for 1, 2, 3 or 4 weeks. In some embodiments, the formulation is taken for 2, 3, 4, 5, 6, 7, 8, 9, 10, 11 or 12 months.

In some embodiments, a daily dose of the formulation can be provided in one or more daily servings. In some embodiments, a daily dose is provided in a single serving. In some embodiments, a daily dose may be provided in two or more servings (up to 5 servings in 24 hours). While the size of each serving may vary, the quantity of active ingredients to be consumed will be equal to one serving. In the case of a single serving, where one single serving is intended to be taken per day, the single serving will comprise a complete daily dose. In the case of multiple servings, the quantity of active ingredients will be such that the total amount of active ingredients in the servings to be taken in a single day is equivalent to a daily dose.

In some embodiments, the formulation is provided in the form of a liquid drink. The liquid drink may comprise the active ingredients in a water base, or in another base liquid that is inert with respect to the active ingredients. The liquid drink may comprise one or more additional inactive ingredients. In some embodiment the liquid drink may comprise one or more gelling or stabilizing agents including, but not limited, to xanthan gum, guar gum, propylene glycol, acacia gum and maltodextrin. In some embodiments the liquid drink may comprise one or more colorants, for example a natural color such as carmine or beet root. In some embodiments the liquid drink may comprise one or more preservatives such as citrus oil, sorbates and benzoates. The liquid drink may also comprise one or more flavors such as fruit (e.g., strawberry, melon, apple, peach, lemon, orange, mango, and the like) and non-fruit flavors. In some embodiments the flavor is a natural flavor. In some embodiments the liquid drink may comprise artificial and natural sweeteners.

In some embodiments the formulation comprises, but is not limited to, one or more artificial sweeteners such as sucralose, acesulfame K or a combination of these and/or one or more natural sweeteners such as sugar, fructose, honey, erythritol, xylitol, stevia, monk fruit, agave, citrus and protein extracts used as sweeteners or combinations thereof.

In some embodiments, the formulation is a liquid drink comprising a single serving of about 4.5 fl. oz. However, the skilled artisan will appreciate that while the size of the serving itself may vary depending on the quantity of the inactive ingredients, such as water, the amount of the active ingredients in each single serving will be within the ranges provided herein. For example, while the single serving size may be ½ fl. oz, 1 fl. oz, 2 fl. oz., 4 fl. oz., 6 fl. oz., 10 fl. oz., 12 fl. oz., 16 fl. oz. or anything smaller or larger, the daily dose of active ingredients will be the same in each serving. In some embodiments a single serving is about 2 fl. oz. to about 54 fl. oz. In some embodiments, the formulation is a liquid concentrate comprising of multiple servings to be diluted into a liquid beverage to obtain a single serving size.

In some embodiments, the formulation is a liquid drink comprising a single serving of about 4.23 fl. oz. (120 grams) (FIG. 1).

In some embodiments, the formulation comprises one or more additional components that improve absorption of one or more of the active ingredients.

In some embodiments, the formulation is taken in the morning on an empty stomach. In some embodiments, the formulation is taken at any time enhanced energy levels are needed. In some embodiments, the formulation is taken daily to provide enhanced energy levels. In some embodiments, the formulation is taken to promote a feeling of overall well-being.

In some embodiments, general health improvements after taking the formulation may include one or more of inhibition, amelioration, delayed onset of, reduced likelihood of, treatment, and/or prevention of metabolic syndrome, and increase in energy levels. In some embodiments, general health improvements after taking the formulation includes include one or more of inhibition, amelioration, delayed onset of, reduced likelihood of, treatment, and/or prevention of metabolic syndrome. In some embodiments, general health improvements after taking the formulation includes increase in energy levels. In some embodiments, general health improvements after taking the formulation includes inhibition, amelioration, delayed onset of, reduced likelihood of, treatment, and prevention of metabolic syndrome, as well as increase in energy levels.

In some embodiments, general health improvements including, but not limited to, inhibition, amelioration, delayed onset of, reduced likelihood of, treatment, and/or prevention of metabolic syndrome, and/or increase in energy levels are observed within 1 day to about 21 days of taking an embodiment of the formulations herein. In some embodiments, general health improvements are observed within 1 day to about 7 days. In some embodiments, general health improvements are observed within 1 day to about 14 days. In some embodiments, general health improvements are observed within 1 day to about 5 days. In some embodiments, general health improvements are observed within 1 day to about 10 days. In some embodiments, general health improvements are observed within 1 day to about 15 days. In some embodiments, general health improvements are observed within 1 day to about 20 days.

In some embodiments, inhibition, amelioration, delayed onset of, reduced likelihood of, treatment, and/or prevention of metabolic syndrome, and increase in energy levels may also be associated with high levels of concentration, optimal cognitive function, effective decision making, keen comprehension, effortless recall, mental clarity, quick reflexes, restful sleep, increased motivation, coordinated motor function, efficient problem solving, mental acuity, optimal energy levels, overall well-being, ability to focus, mood stability, memory support, alertness, improved neurotransmission, and nerve cell integrity.

In some embodiments, the formulations may provide benefits to subjects suffering from other conditions related to metabolic syndrome and lower energy levels. Non-limiting examples include Post Traumatic Stress Disorder (PTSD), Attention Deficit Disorder (ADD), Attention Deficit Hyperactivity Disorder (ADHD), anxiety, migraine, dementia, tinnitus, and in hangovers.

In some embodiments, formulations comprising combinations of Tart cherry, Vitamin C, Turmeric (20% w/w Curcumin), Inulin, and Grape seed extract are provided. In some embodiments, formulations comprising sub-combinations of Tart cherry, Vitamin C, Turmeric (Curcumin), Inulin, and Grape seed extract are provided. In some embodiments, the combinations and sub-combinations further comprise Inosine. In some embodiments, the combinations and sub-combinations further comprise creatine. In some embodiments, the combinations and sub-combinations further comprise Inosine and creatine.

In some embodiments, the combinations and sub-combinations are intended to target and utilize multiple biochemical pathways and entry points for energy (ATP) production. For example, tart cherry can inhibit Xanthine Oxidase of the salvage pathway, Curcumin, grape seed, and Tart cherry can cause AMPK activation (i.e., activate classical TCA cycle pathway, Inosine can enhance the salvage pathway, Creatine provides extra substrate for final ATP production, and the anti-inflammatory properties tart cherry, grape seed, and curcumin can save and conserve energy.

In some embodiments, the ingredients in the combinations and sub-combinations act synergistically to amplify the effect of formulation in inhibiting, ameliorating, delaying the onset of, reducing the likelihood of, treating, and/or preventing metabolic syndrome, and/or increasing energy levels by affecting more than one physiological targets via independent mechanisms. For example, without being limited by any particular theory, Tart Cherry can lower uric acid levels, as well as indirectly increase AMPK and NO as well as reduce inflammation via cox pathway, Vitamin C can increase excretion of uric acid and anti-oxidant, Curcumin can directly increase AMPK and anti-inflammatory, the anti-oxidant resveratrol in Grape seed extract can act against insulin resistance, and Inulin, a prebiotic, can mitigate metabolic syndrome.

Without being limited by any particular theory, while uric acid's contribution to metabolic syndrome is still emerging, lowering uric acid is for the most part restricted to treating gout (very high levels of uric acid that precipitate an arthritis). In some embodiments, the formulations herein can provide the advantage of lowering uric acid even from the "normal range" to improve metabolic function including normalizing blood pressure, lipids, fat storage, insulin resistance, etc. The amount of lowering uric acid even mildly is likely to induce changes in metabolic function in a far more effective way than the original gout treatment. In some embodiments, the formulations can be used in combination with other drugs that are currently used. As a result, potentially synergistic effects can be achieved. For example, the formulations herein can be combined with metformin, which is one of the treatments for insulin resistance. Lowering uric acid can lower gout. In some embodiments, Vitamin C in the formulation further lowers uric acid by alternative mechanisms and has a synergistic. In some embodiments, Curcumin and grape seed extract further promote metabolic health from alternative pathways and provide synergistic effects. In some embodiments, the anti-inflammatory properties of tart cherry address another concurrent pathological pathway (inflammation) which is connected to obesity. In some embodiments, the formulations herein can be used to improve access to the body's natural energy stores and improve endurance and performance. In some embodiments, the additional anti-inflammatory properties of the formulations disclosed herein can be also used in recovery from exercise or injury. In some embodiments, the formulations can be used as an energy and health supplement.

In some embodiments, the formulation comprises at least 4 active ingredients that are synergistic in their effects. In some embodiments, the formulation comprises at least 4, 5, 6, 7, 8, 9, 10, 11, 12 or 13 synergistic active ingredients. For example, the active ingredients may be synergistic with respect to their positive effects with respect to inhibiting, ameliorating, delaying the onset of, reducing the likelihood of, treating, and/or preventing metabolic syndrome, and/or increasing energy levels.

In some embodiments, the effects of 4 or more of the active ingredients are additive. In some embodiments, the effects of at least 4, 5, 6, 7, 8, 9, 10, 11, 12 or 13 of the active ingredients are additive. For example, the effects may be additive with respect to having positive effects with respect to inhibiting, ameliorating, delaying the onset of, reducing the likelihood of, treating, and/or preventing metabolic syndrome, and/or increasing energy levels.

In some embodiments, the effects of the at least 4-13 active ingredients are additive. In some embodiments, the effects of the at least 4-13 active ingredients are synergistic. In some embodiments, the effects of the at least 4-13 active ingredients are additive and/or synergistic.

In some embodiments, the formulations comprise about 1500 mg of Tart cherry. In some embodiments, the formulations comprise about 250 mg to about 2500 mg of Tart cherry. In some embodiments, the formulations comprise about 500 mg to about 5000 mg of Tart cherry. In some embodiments, the formulations comprise about 750 mg to about 7500 mg of Tart cherry. In some embodiments, the formulations comprise about 1000 mg to about 15000 mg of Tart cherry.

In some embodiments, the formulations comprise about 250 mg of Vitamin C. In some embodiments, the formulations comprise about 25 mg to about 500 mg of Vitamin C. In some embodiments, the formulations comprise about 100 mg to about 1000 mg of Vitamin C. In some embodiments, the formulations comprise about 200 mg to about 2000 mg of Vitamin C. In some embodiments, the formulations comprise about 500 mg to about 2500 mg of Vitamin C.

In some embodiments, the formulations comprise about 25 mg Turmeric (20% w/w Curcumin). In some embodiments, the formulations comprise about 2.5 mg to about 10 mg Turmeric (20% w/w Curcumin). In some embodiments, the formulations comprise about 5 mg to about 50 mg Turmeric (20% w/w Curcumin). In some embodiments, the formulations comprise about 25 mg to about 125 mg Turmeric (20% w/w Curcumin). In some embodiments, the formulations comprise about 100 mg to about 250 mg Turmeric (20% w/w Curcumin).

In some embodiments, the formulations comprise about 500 mg of Inulin. In some embodiments, the formulations comprise about 50 mg to about 350 mg of Inulin. In some embodiments, the formulations comprise about 300 mg to about 1500 mg of Inulin. In some embodiments, the formulations comprise about 2000 mg to about 3500 mg of Inulin. In some embodiments, the formulations comprise about 3500 mg to about 5000 mg of Inulin.

In some embodiments, the formulations comprise about 200 mg Grape seed extract. In some embodiments, the formulations comprise about 20 mg to about 500 mg Grape seed extract. In some embodiments, the formulations comprise about 250 mg to about 750 mg Grape seed extract. In some embodiments, the formulations comprise about 500 mg to about 1500 mg Grape seed extract. In some embodiments, the formulations comprise about 1000 mg to about 2000 mg Grape seed extract.

In some embodiments, the formulation comprises the following active ingredients in the indicated recommended amounts in one dose or serving of the formulation, for example in a daily dose:

Tart cherry extract—about 0.25 gm/day to about 5 gm/day. Without being limited by any particular theory, this dosage is equivalent to about 180 Montmorency cherries.

Vitamin C—0 gm/day to about 2 gm/day

Curcumin—0 gm/day to about 2 gm/day.

Grape seed oil extract—about 0 mg/day to about 300 mg/day.

Inulin—0 gm/day to about 10 gm/day.

In some embodiments, the formulations comprise Tart cherry extract at a dose range of about 0.25 gm to about 5 gm per daily dose or serving.

In some embodiments, the formulations comprise Vitamin C at a dose range of about 0 gm to about 2 gm per daily dose or serving.

In some embodiments, the formulations comprise Curcumin at a dose range of about 0 gm/to about 2 gm per daily dose or serving.

In some embodiments, the formulations comprise Grape seed oil extract at a dose range of about 0 mg to about 300 mg per daily dose or serving.

In some embodiments, the formulations comprise Inulin at a dose range of about 0 gm to about 10 gm per daily dose or serving.

In some embodiments of the formulation, an effective amount of the at least one extract from a tart cherry ranges from about 1.5 grams to about 2.5 grams. In some embodiments of the formulation, an effective amount of the at least one extract from a tart cherry ranges from about 0.15 gram to about 25 grams.

In some embodiments of the formulation, an effective amount of the at least one antioxidant vitamin ranges from about 250 mg to about 500 mg. In some embodiments of the formulation, an effective amount of the at least one antioxidant vitamin ranges from about 25 mg to about 5000 mg.

In some embodiments of the formulation, an effective amount of the at least one polyphenolic compound ranges from about 25 mg to about 200 mg. In some embodiments of the formulation, an effective amount of the at least one polyphenolic compound ranges from about 2.5 mg to about 2000 mg.

In some embodiments of the formulation, an effective amount of the at least one prebiotic is about 450 mg. In some embodiments of the formulation, an effective amount of the at least one prebiotic ranges from about 45 mg to about 4500 mg.

In some embodiments, an effective amount of Tart cherry extract in the formulation ranges from about 0.15 gram to about 25 grams. In some embodiments, an effective amount of Tart cherry extract in the formulation ranges from about 1.5 grams to about 2.5 grams.

In some embodiments, an effective amount of Vitamin C in the formulation ranges from about 25 mg to about 5000 mg. In some embodiments, an effective amount of Vitamin C in the formulation ranges from about 250 mg to about 500 mg.

In some embodiments, an effective amount of Grape seed extract in the formulation ranges from about 20 mg to about 2000 mg. In some embodiments, an effective amount of Grape seed extract is about 200 mg.

In some embodiments, an effective amount of Turmeric in the formulation ranges from about 2.5 mg to about 250 mg. In some embodiments, an effective amount of Turmeric in the formulation is about 25 mg.

In some embodiments, an effective amount of Inulin in the formulation ranges from about 45 mg to about 4500 mg. In some embodiments, an effective amount of Inulin in the formulation is about 450 mg.

Any one or more of the embodiments of the formulations and kits of formulations disclosed herein can be used in methods for inhibiting, ameliorating, delaying the onset of, reducing the likelihood of, treating, and/or preventing metabolic syndrome, and/or increasing energy levels.

Any one or more of the embodiments of the formulations and kits of formulations disclosed herein can be used in methods for inhibiting, ameliorating, delaying the onset of, reducing the likelihood of, treating, and/or preventing metabolic syndrome.

Any one or more of the embodiments of the formulations and kits of formulations disclosed herein can be used in methods for increasing energy levels.

Methods of Making Formulations

Also disclosed herein are embodiments of methods of making any of the formulations disclosed herein.

In some embodiments, methods are described for making the embodiments of the formulations herein, wherein the formulations comprise one or more ingredients that are prone to floatation, sedimentation, and/or precipitation. In some embodiments, methods of making a liquid dietary supplement drink using a combination of synergistic ingredients that target long and short-term human brain health are described in which the formation of floaties (precipitate) or bottom-settlement (sediment) in the formulation is reduced or avoided entirely.

In some embodiments, the generation of a sediment and/or precipitate can be reduced or avoided by combining the ingredients in one or more particular sequences. Thus, in some embodiments special attention is given to the order in which each ingredient is added. In particular, in some embodiments the ingredients are added in an order which results in all of the ingredients going into solution, or staying in suspension.

In addition to avoiding precipitation and sedimentation, other indicators of stability of the formulation can be preserved during preparation of the formulation. These indicators of stability of the formulation may include, for example, flavor profile, texture and mouth-feel. Thus, in some embodiments, one or more indicator of stability, such as flavor profile, texture and mouth-feel of the formulation prepared according to the methods described herein are substantially as desired.

In some embodiments, the ingredients are freeze dried to create a powder that minimizes loss of potency before preparing a formulation.

In some embodiments, any of the ingredients in the formulations can be the first ingredient to be added to water or other liquid in preparing a liquid formulation. The remaining ingredients may be added in any order or combination. Flavor components, colorants and sweeteners, if any, are typically added last.

In some embodiments, tart cherry extract is the first ingredient that is added to water or other liquid in preparing a liquid formulation. The remaining ingredients may be added in any order or combination.

In some embodiments, Vitamin C is the first ingredient that is added to water or other liquid in preparing a liquid formulation. The remaining ingredients may be added in any order or combination.

In some embodiments, Curcumin is the first ingredient that is added to water or other liquid in preparing a liquid formulation. The remaining ingredients may be added in any order or combination.

In some embodiments, grape se extract is the first ingredient that is added to water or other liquid in preparing a liquid formulation. The remaining ingredients may be added in any order or combination.

In some embodiments, inulin is the first ingredient that is added to water or other liquid in preparing a liquid formulation. The remaining ingredients may be added in any order or combination.

In some embodiments, the formulation is prepared in the form of a liquid drink. The liquid drink may comprise the active ingredients in a water base, or in another base liquid that is inert with respect to the active ingredients. The liquid drink may comprise one or more additional inactive ingredients. In some embodiments the liquid drink may comprise one or more preservatives such as citrus oil, sorbates and benzoates. The liquid drink may also comprise one or more flavors such as fruit (e.g., strawberry, melon, apple, peach, lemon, orange, mango, and the like) and non-fruit flavors. In some embodiments the flavor is a natural flavor.

In some embodiments, sweeteners, such as sucralose or acesulfame K or a combination thereof, are added. In some embodiments, a natural sweetener such as sugar, fructose, honey, agave, monk fruit, stevia, erythritol, xylitol, citrus and protein extracts or a combination thereof are added.

In some embodiments, a liquid formulation is prepared by combining the following water, tart cherry extract, vitamin, curcumin, grape seed extract, and inulin. In some embodiments, inosine is optionally added. In some embodiments, creatine is optionally added. In some embodiments, inosine and creatine are optionally added.

In some embodiments, the ingredients are mixed in an order that allows for optimum solubility throughout the liquid phase. In some embodiments, the ingredients are mixed in an order that does not interfere with the dispersion and solubility of other ingredients throughout the liquid phase and does not, for example, lead to clumps (precipitation) and/or fall-out (sedimentation) throughout the liquid. In some embodiments, the ingredients are mixed in a specific order that is empirically determined and that allows for optimum solubility throughout the liquid phase. In some embodiments, the ingredients are mixed in an order that is empirically determined and that does not interfere with the dispersion and solubility of other ingredients throughout the liquid phase and does not, for example, lead to clumps (precipitation) and/or fall-out (sedimentation) throughout the liquid.

In some embodiments, one or more additional ingredients are added to water one or more premixes, each premix comprising a fraction of the other ingredients. The premixes may be added in multiple steps or in a single step.

In some embodiments, all additional ingredients are added to water as a single premix comprising all the additional ingredients.

In some embodiments, the time required for dissolving and/or dispersing the ingredients in water at least about 10 to about 60 minutes. In some embodiments, the time required is about 10 to about 30 minutes. In some embodiments, the time required is about 20 to about 60 minutes.

In some embodiments, additional flavoring components are added to the formulation. In some embodiments, any and all flavoring components, such as Natural flavors, and sweeteners are added next, either individually and sequentially any order, or simultaneously. Exemplary sweeteners include, but are not limited to natural sweeteners, such as Sugar, Fructose, Honey, Agave, Monk fruit, Stevia, Erythritol, Xylitol, Citrus and Protein extracts, and artificial sweeteners such as Sucralose, Acesulfame K, or a combination of these.

The ingredients and flavoring components may be dissolved in the solution, for example, by one or more of the following techniques: gentle stirring, gentle vortexing, gentle heating. In some embodiments, the time required for dissolving these components is at least about 5 to about 60 minutes. In some embodiments, the time required is about 5 to about 30 minutes. In some embodiments, the time required is about 30 to about 60 minutes.

In some embodiments colorant or colorants are added next and dissolved in the solution, for example, by one or more of the following techniques: gentle stirring, gentle vortexing, gentle heating. In some embodiments, the time required for dissolving these components is at least about 5 to 20 minutes. In some embodiments, the time required is about 30 minutes to about 50 minutes.

In some embodiments one or more salts are added next and dissolved in the solution, for example, by one or more of the following techniques: gentle stirring, gentle vortexing, gentle heating. In some embodiments, the time required for dissolving the one or more salts is at least about 5 to 20 minutes. In some embodiments, the time required is about 30 minutes to about 50 minutes.

In some embodiments, the pH of the finished product is acidic. In some embodiments, the pH of the finished product is about 3 to about 6.5. In some embodiments, the pH of the finished product is about 3.0, 3.5, 4.0, 4.5, 5.0, 5.5, 6.0, or 6.5.

In some embodiments, the formulation comprises at least 4 active ingredients that are synergistic in their effects. In some embodiments, the formulation comprises at least 4, 5, 6, 7, 8, 9, 10, 11, 12 or 13 synergistic active ingredients. For example, the active ingredients may be synergistic with respect to their positive effects with respect to inhibiting, ameliorating, delaying the onset of, reducing the likelihood of, treating, and/or preventing metabolic syndrome, and/or increasing energy levels.

In some embodiments, the methods result in formulations that comprise about 1500 mg of Tart cherry. In some embodiments, the methods result in formulations that about 250 mg to about 2500 mg of Tart cherry. In some embodiments, the methods result in formulations that about 500 mg to about 5000 mg of Tart cherry. In some embodiments, the methods result in formulations that comprise about 750 mg to about 7500 mg of Tart cherry. In some embodiments, the formulations comprise about 1000 mg to about 15000 mg of Tart cherry.

In some embodiments, the methods result in formulations that comprise about 250 mg of Vitamin C. In some embodiments, the methods result in formulations that comprise about 25 mg to about 500 mg of Vitamin C. In some embodiments, the methods result in formulations that comprise about 100 mg to about 1000 mg of Vitamin C. In some embodiments, the methods result in formulations that comprise about 200 mg to about 2000 mg of Vitamin C. In some embodiments, the methods result in formulations that comprise about 500 mg to about 2500 mg of Vitamin C.

In some embodiments, the methods result in formulations that comprise about 25 mg Turmeric (20% w/w Curcumin). In some embodiments, the methods result in formulations that comprise about 2.5 mg to about 10 mg Turmeric (20% w/w Curcumin). In some embodiments, the methods result in formulations that comprise about 5 mg to about 50 mg Turmeric (20% w/w Curcumin). In some embodiments, the methods result in formulations that comprise about 25 mg to about 125 mg Turmeric (20% w/w Curcumin). In some embodiments, the methods result in formulations that comprise about 100 mg to about 250 mg Turmeric (20% w/w Curcumin).

In some embodiments, the methods result in formulations that comprise about 500 mg of Inulin. In some embodiments, the methods result in formulations that comprise about 50 mg to about 350 mg of Inulin. In some embodiments, the methods result in formulations that comprise about 300 mg to about 1500 mg of Inulin. In some embodiments, the methods result in formulations that comprise about 2000 mg to about 3500 mg of Inulin. In some embodiments, the methods result in formulations that comprise about 3500 mg to about 5000 mg of Inulin.

In some embodiments, the methods result in formulations that comprise about 200 mg Grape seed extract. In some embodiments, the methods result in formulations that comprise about 20 mg to about 500 mg Grape seed extract. In some embodiments, the methods result in formulations that comprise about 250 mg to about 750 mg Grape seed extract. In some embodiments, the methods result in formulations that comprise about 500 mg to about 1500 mg Grape seed extract. In some embodiments, the methods result in formulations that comprise about 1000 mg to about 2000 mg Grape seed extract.

In some embodiments, the methods result in a formulation that comprises the following active ingredients in the indicated recommended amounts in one dose or serving of the formulation, for example in a daily dose:

Tart cherry extract—about 0.25 gm/day to about 5 gm/day. Without being limited by any particular theory, this dosage is equivalent to about 180 Montmorency cherries.

Vitamin C—0 gm/day to about 2 gm/day

Curcumin—0 gm/day to about 2 gm/day.

Grape seed oil extract—about 0 mg/day to about 300 mg/day.

Inulin—0 gm/day to about 10 gm/day.

In some embodiments, the methods result in formulations that comprise Tart cherry extract at a dose range of about 0.25 gm to about 5 gm per daily dose or serving.

In some embodiments, the methods result in formulations that comprise Vitamin C at a dose range of about 0 gm to about 2 gm per daily dose or serving.

In some embodiments, the methods result in formulations that comprise Curcumin at a dose range of about 0 gm/to about 2 gm per daily dose or serving.

In some embodiments, the methods result in formulations that comprise Grape seed oil extract at a dose range of about 0 mg to about 300 mg per daily dose or serving.

In some embodiments, the methods result in formulations that comprise Inulin at a dose range of about 0 gm to about 10 gm per daily dose or serving.

In some embodiments the methods result in a formulation that is a single serving to be taken once per day by a subject. Thus, in some embodiments a daily dose of active ingredients is provided in a single serving. In some embodiments one daily dose may be divided among two or more servings to be taken in a day, for example among two or more servings of a liquid beverage or two or more tablets. A daily dose of the formulation is preferably taken by or administered to a subject in a 24-hour period. In some embodiments, a daily dose of the formulation is taken every day for 1 week to 12 months. In some embodiments, the formulation is taken for 1, 2, 3 or 4 weeks. In some embodiments, the formulation is taken for 2, 3, 4, 5, 6, 7, 8, 9, 10, 11 or 12 months.

In some embodiments, the methods result in a formulation that is to be taken in the morning on an empty stomach. In some embodiments, the methods result in a formulation that is to be taken at any time mental focus and clarity is needed. In some embodiments, the methods result in a formulation that is to be taken daily to promote brain health. In some embodiments, the methods result in a formulation that is to be taken to promote restful sleep. In some embodiments, the methods result in a formulation that is to be taken to promote a feeling of overall well-being.

In some embodiments, the methods result in a liquid drink formulation such that a single serving of the liquid drink formulation comprises about 4.5 fl. oz. However, the skilled artisan will appreciate that while the size of the serving itself may vary depending on the quantity of the inactive ingredients, such as water, the amount of the active ingredients in each single serving will be within the ranges provided herein. For example, while the single serving size may be ½ fl. oz., 1 fl. oz., 2 fl. oz., 4 fl. oz., 6 fl. oz., 10 fl. oz., 12 fl. oz., 16 fl. oz. or anything smaller or larger, the daily dose of active ingredients will be the same in each serving. In some embodiments a single serving is about 2 fl. oz. to about 54 fl. oz. In some embodiments, the formulation is a liquid concentrate comprising of multiple servings to be diluted into a liquid beverage to obtain a single serving size.

In some embodiments, the methods result in a liquid drink formulation comprising a single serving of about 4.23 fl. oz. (120 grams) (FIG. 1).

In some embodiments of the methods, the product is cold filled. In some embodiments of the methods, the product is pasteurized. In some embodiments of the methods, the product is pasteurized and/or cold filled.

Kits of Formulations

In some embodiments, a kit is provided which comprises a formulation or combination or subcombination according to any of the embodiments disclosed herein and a dietary plan comprising instructions to use of the formulation in the kit for inhibiting, ameliorating, delaying the onset of, reducing the likelihood of, treating, and/or preventing metabolic syndrome, and/or increasing energy levels. In some embodiments, the dietary plan comprises taking at least one serving of a formulation provided herein per day, for example in the form of a liquid beverage. In some embodiments, the dietary plan can comprise taking at least one serving of a formulation provided herein per day, for example in the form of a liquid beverage of about 4.5 fl. oz. In some embodiments, at least one serving can be taken in the morning on an empty stomach. In some embodiments, at least one serving can be taken at any time, for example, when increased energy levels are desired (e.g., during a workout, during a marathon, etc.).

In some embodiments, at least two servings can be taken at any time. In some embodiments, a maximum of five servings in a 24-hour period can be taken. In some embodiments, at least 1, 2, 3, 4, or 5 servings can be taken at any time. In some embodiments, the servings are effective in inhibiting, ameliorating, delaying the onset of, reducing the likelihood of, treating, and/or preventing metabolic syndrome, and/or increasing energy levels.

In some embodiments, the kit comprises a formulation in the kit is an edible solid or an edible semi-solid. In some embodiments, the formulation in the kit is a potable liquid. In some embodiments, the formulation in the kit is a powder or pellet that can be reconstituted in a potable liquid (e.g., water). In some embodiments, the formulation in the kit is a tablet or a capsule that can be taken without reconstitution.

EXAMPLES

The following examples are non-limiting and other variants within the scope of the art also contemplated.

Examples 1-10 provide anecdotal reports of the effect on volunteers of the embodiments of the natural formulations disclosed herein. For all the volunteers, one dosage a day was administered (4 gm of product/formulation), which comprised 1.5 grams cherry extract, 250 mg Vitamin C, 200 mg grape skin extract, and 25 mg Turmeric—otherwise referred in the Examples as Ten Plus.

Example 1—Karen S

This study involved a 56 year old female volunteer, whose routine included regular exercises with tennis and Pilates 4-5 times per week. Within one week of starting an embodiment of the formulations disclosed herein (called Ten Plus), she noticed extra stamina and endurance in both tennis performance and Pilates routine. She ran out of her supply for 2-3 days and noticed a dramatic fall in her energy and performance levels. She recovered energy when starting to use Ten Plus again.

Example 2—Tommy S

This study involved a 57 year old male volunteer, who regular routine included exercise with Tennis and Pilates with Karen S, and who had a similar experience using Ten Plus for one week. He had a surge in energy and focus while using Ten Plus and had less energy when not using the formulation.

Example 3—Jon T

This study involved a 52 year old male volunteer. After one week of using Ten Plus, he noticed extra stamina and endurance in every day activity.

Example 4—Lonnie M

This study involved a 64 year old male volunteer. After one week of using Ten Plus, there were very noticeable changes in energy levels and focus.

Example 5—Adrianna P

This study involved an: 86 year old female volunteer. After three weeks of using Ten Plus, a dramatic increase in energy and stamina was observed. Also, a remarkable drop in C-reactive protein (CRP) and sedimentation rate was observed since using Ten Plus. Prior to taking Ten Plus, her base line level of CRP was 14 mg/L, and her base line sedimentation rate was 55 mm/h. After three weeks of using Ten Plus, the CRP level decreased to 10 mg/L, and sedimentation rate decreased to 20 mm/h.

Example 6—David B

This study involved a 75 year old male volunteer. After two weeks of using Ten Plus, a strong increase in energy and endurance was observed.

Example 7—Jay B

This study involved a 35 year old male volunteer. After one week of using Ten Plus, a dramatic improvement in endurance and focus in work outs was observed.

Example 8—Arthur A

This study involved a 27 year old male volunteer. After two to three days of using Ten Plus, a very strong increase in energy and endurance in workouts and general stamina.

Example 9—Megan K

This study involved a 45 year old female volunteer, who has been lifelong athlete and rigorous workout enthusiast. After three days of using Ten Plus, she noticed a dramatic increase in energy levels.

Example 10—Chani K. Krich

This study involved a 40 year old female volunteer. After three days of using Ten Plus, she noticed a dramatic increase in endurance and energy and focus.

REFERENCES

All references cited herein are incorporated by reference in their entireties

Hirsch et al 2012: Allopurinol infusion showed increase ATP and ATP flux in a double blinded study in cardiac patients.

Kamatani et al 2017: Showed Febuxotat+inosine oral ingestion increased cell ATP more than Febuxostat alone. While Inosine alone had no effect on ATP.

Johnson et al 2019: review article concerning increase ATP and how Xanthine oxidase inhibition increase ATP through purine salvage.

*Journal of functional foods* 11 (2014) 82-90 Phillip G. Bell, David C. Gaze, Gareth W. Davison, Trevor W. George, Michael J. Scotter, Glyn Howatson.

*Journal of Medicinal Food Vol* 12 issue 9 26 Oct. 2009 Regular Tart Cherry Intake Alters Abdominal Adiposity, Adipose Gene Transcription, and Inflammation in Obesity-Prone Rats Fed a High Fat Diet, E. M. Seymour, Sarah K. Lewis, Daniel E. Urcuyo-Llanes, Ignasia I. Tanone, Ara Kirakosyan, Peter B. Kaufman, and Steven F. Bolling.

Nutrition & Food Science Vol. 38 No. 4, 2008 pp. 355-360 *Scand J Med Sci Sports.* 2018 July; 28(7):1746-1756. Epub 2018 Apr. 16.

*European Journal of Applied Physiology* March 2019, Volume 119, *Issue* 3, pp 675-6841 Montmorency cherry supplementation improves 15-km cycling time-trial performance

What is claimed is:

1. A method for increasing energy levels in a subject, the method comprising:
   increasing or activating AMPK in the subject by administering to the subject an effective amount of a formulation comprising:
   about 500 mg of at least one extract from a tart cherry (*prunus cerasus*), wherein the at least one extract from a tart cherry inhibits xanthine oxidase to both (1) block the conversion, and cause increased accumulation of, hypoxanthine and xanthine, thereby increasing the purine salvage pathway, leading to an increase in AMP, which activates AMPK and causes an increase in ATP, and (2) reduce uric acid levels, thereby decreasing inhibition of AMPK by uric acid, increasing AMPK, and increasing ATP;
   an effective amount of about 25 mg to about 500 mg of Vitamin C, wherein the Vitamin C reduces uric acid by increasing excretion of uric acid to synergistically, with the at least one extract from a tart cherry, increase energy levels in the subject.

2. The method of claim 1, wherein the effective amount of Vitamin C ranges from about 25 mg to about 250 mg.

3. The method of claim 1, wherein the formulation is administered to the subject once per day.

4. The method of claim 1, wherein the formulation is administered to the subject as an edible solid or edible semi-solid.

5. The method of claim 1, wherein the formulation further comprises curcumin.

6. The method of claim 1, wherein the at least one extract from a tart cherry is from Montmorency cherries.

* * * * *